United States Patent [19]
Fischell

[11] Patent Number: 5,180,376
[45] Date of Patent: Jan. 19, 1993

[54] NON-BUCKLING THIN-WALLED SHEATH FOR THE PERCUTANEOUS INSERTION OF INTRALUMINAL CATHETERS

[75] Inventor: Robert E. Fischell, Dayton, Md.

[73] Assignee: Cathco, Inc., Dayton, Md.

[21] Appl. No.: 517,213

[22] Filed: May 1, 1990

[51] Int. Cl.$^5$ .............................................. A61M 25/00
[52] U.S. Cl. .................................... 604/282; 604/169; 128/658; 138/130; 138/133
[58] Field of Search ............... 604/282, 95, 283, 169, 604/244, 280-281, 264; 128/772, 656-658; 138/129, 131-134, 130, 139

[56] References Cited

U.S. PATENT DOCUMENTS

| | | | |
|---|---|---|---|
| 3,190,084 | 6/1965 | Moon et al. | 138/131 |
| 3,802,433 | 4/1974 | Raven | 604/283 |
| 4,044,765 | 8/1977 | Kline | 604/282 |
| 4,052,989 | 10/1977 | Kline | 604/282 |
| 4,240,411 | 12/1980 | Hosono | 128/4 |
| 4,411,655 | 10/1983 | Schreck | 604/281 |
| 4,610,674 | 9/1986 | Suzuki et al. | 604/282 |
| 4,636,346 | 1/1987 | Gold et al. | 604/280 |
| 4,676,229 | 6/1987 | Krasnicki et al. | 604/282 |
| 4,690,175 | 9/1987 | Ouchi et al. | 604/282 |
| 4,705,511 | 11/1987 | Kocak | 604/282 |
| 4,863,442 | 9/1989 | DeMello et al. | 604/282 |
| 4,895,168 | 1/1990 | Machek | 128/772 |
| 4,917,666 | 4/1990 | Solar et al. | 604/95 |
| 4,936,845 | 6/1990 | Stevens | 606/180 |
| 4,955,862 | 9/1990 | Sepetka | 128/658 |

FOREIGN PATENT DOCUMENTS 0198962 10/1986 European Pat. Off. ............ 604/283

*Primary Examiner*—C. Fred Rosenbaum
*Assistant Examiner*—Mark W. Bockelman

[57] ABSTRACT

An introducer sheath includes an extremely thin, flat wire metal coil that is surrounded only on its exterior surface with a plastic tube or coating. The flat wire coil optimizes the resistance of the sheath to buckling while minimizing the wall thickness of the sheath. The plastic covering being only on the outside of the metal coil optimizes the thinness of the introducer sheath wall while still providing a smooth outer surface for easy percutaneous insertion into an artery or other vessel of a living body. The higher density of the metal coil as compared to the plastic tubes of existing introducer sheaths, maximizes the radiopacity of the sheath for this thin-walled design. An alternative embodiment consists of two flat wire metal coils, one wound over the other, with a plastic covering the outer surface of the outer metal coil.

8 Claims, 1 Drawing Sheet

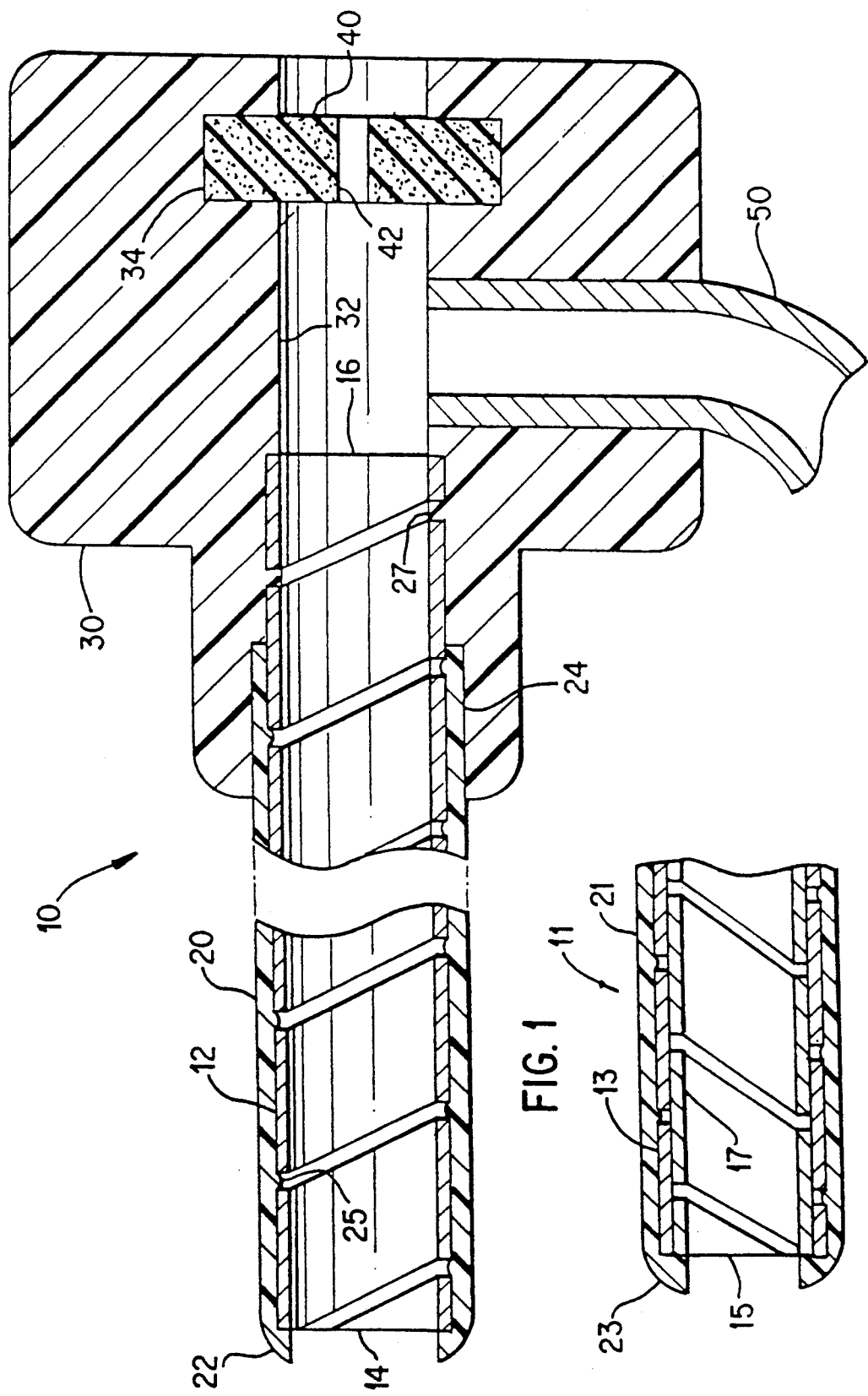

NON-BUCKLING THIN-WALLED SHEATH FOR THE PERCUTANEOUS INSERTION OF INTRALUMINAL CATHETERS

FIELD OF THE INVENTION

This invention is in the field of sheaths that pass through the skin and then enter an artery or any other vessel in a living body for the purpose of percutaneous insertion of transluminal catheters.

BACKGROUND OF THE INVENTION

It is common practice in the fields of angioplasty and atherectomy to insert catheters into the artery through a plastic sheath. These sheaths are typically made from PVC or an equivalent plastic and have a wall thickness which is typically 10 mils. The difficulty with existing sheaths is that they are so thin-walled and made from plastic so that they occasionally buckle at the point where they enter into or bend in the femoral artery.

It is highly advantageous to make the sheath as thin-walled as is possible. The inner diameter of a sheath has a dimension which is controlled by the outside diameter of the catheter to be placed through it. The outside diameter of the sheath is then typically 20 mils greater then the inside diameter in order to provide a 10 mil wall of plastic which is necessary to give the sheath adequate strength. However, it would be highly advantageous to reduce the outside diameter of the sheath so as to minimize arterial distension thereby reducing the bleeding that occurs at the insertion site after the catheter and sheath are removed from the artery.

Because they are made from a thin-walled plastic, current sheaths are not radiopaque. However, it would be highly advantageous to have a radiopaque sheath so that the placement of its distal end in a vessel could be ascertained by fluroscopy.

SUMMARY OF THE INVENTION

It is the goal of the present invention to eliminate the shortcomings of the prior art devices in order to provide a radiopaque sheath that is non-buckling and with a thinner wall as compared with sheathes that are currently available. To achieve both a thinner wall for the sheath and to avoid buckling, this invention uses a helical metal coil for its interior which most advantageously would be fabricated from flat wire. A thin plastic covering could be coated onto the metal coil or the covering might be attached using heat shrinkable tubing, or by molding or extruding plastic over the thin helical metal coil. At the proximal end of the sheath the adapter through which the catheters are to be placed would typically be molded from a plastic so as to both join onto the metal coil as well as mold onto the plastic covering of the metal coil.

Thus it is an object of this invention to provide a sheath design which will preclude buckling. It is further an objective of this invention to have a non-bucking sheath whose wall thickness is considerably reduced compared to the 10 mil wall thickness that is available in the devices that are now being used with balloon angioplasty catheters or atherectomy catheters.

It is a still further objective of this invention to have a thin-walled sheath that is radiopaque.

BRIEF DESCRIPTION OF THE DRAWING

FIG. 1 is a cross-sectional view of a non-buckling thin-walled sheath with a single helical metal coil.

FIG. 2 is a cross-sectional view of the distal end of a non-buckling sheath which has two helical metal coils.

DETAILED DESCRIPTION OF THE INVENTION

As can be seen in FIG. 1, a non-buckling, thin-walled sheath 10 is shown with an inner metal coil 12 that lies within a plastic covering 20 for most of the length of the sheath with a plastic adaptor 30 molded on to the proximal end of the sheath 10. The metal coil 12 would typically be fabricated from flat stainless steel wire or an equivalent springy metal. The thickness of the wire would typically lie between 1 and 5 mils and the width of the wire would typically be between 5 to 50 times the wire thickness. The flat wire would typically be wound on a mandril in a similar manner to the way that spring wire guides are made at the present time. The inner diameter of the helical coil would typically lie between 40 mils and 200 mils depending on the size of the catheter that has to be inserted through it. The distal end 14 and the proximal distal end 16 of the coil 12 would be cut off square as shown in FIG. 1.

Covering the helical coil 12 would be a plastic covering 20 which would typically be made from polyethylene, polyurethane, PVC or a similar plastic material. One method for forming the covering 20 so that it fits tightly around the helical coil 12 would be by sliding the coil 12 through a tube of the plastic and then heat shrinking the plastic onto the helical coil 12. Another method would be to dip coat the coil 12 into a liquid plastic material that hardens onto the helical coil 12 after dipping. Whatever method is used to form the plastic covering 20, the plastic material would have an unfilled extension 25 or a filled extension 27 each of which projects into the space between adjacent turns of the coil. This type of structure maintains a forced separation between adjacent turns thereby preventing unwanted longitudinal displacement of one turn relative to another when the sheath 10 is severely bent. The inside diameter of either extension 25 or 27 is smaller that the outside diameter of the metal coil 12 and larger than or equal to the inside diameter of the metal coil 12.

In FIG. 1 we see that the distal tip 22 of the plastic covering 20 might be heat molded to an appropriate shape which can readily pass through the arterial wall with the aid of an introducer. The proximal end 24 of the covering 20 would have molded onto it a plastic adapter 30 which can have a side-port 50 as shown in FIG. 1. The adapter 30, which may be formed from the same plastic material as the covering 20 or from another material such as PVC, would also be molded onto the proximal end of the helical coil 12. The adapter 30 would have an interior cylindrical hole 32 whose inside diameter is molded to match the inside diameter of the helical coil 12. A cylindrical groove 34 would be molded into the adapter 30 so as to accept a foam rubber packing gland 40. The packing gland 40 has a hole 42 through its center to allow for the passage of a catheter. The purpose of the gland 40 is to seal around the outside diameter of the catheter when it is in place to prevent arterial blood from escaping between the inner cylinder 32 of the adapter 30 and the outside diameter of the catheter that is percutaneously placed into the arterial system.

As previously described, the helical coil 12 would have a wall thickness of the metal that lies between 1 and 5 mils. Similarly the plastic covering 20 would have a wall thickness that lies between 1 and 5 mils. As a result, the total thickness of the coil 12 and covering 20 would be between 2 and 10 mils. At 10 mils thickness, the sheath would have the advantage of being non-buckling. However, it would not have any advantage in reducing the outer diameter of the sheath 10 as compared to other sheaths that are currently available. However, as we approach wire and plastic covering thicknesses on the order of 2 mils, the outer diameter of the sheath 10 is significantly reduced. There is a distinct advantage in dramatically reducing the wall thickness of the sheath 10 while at the same time having improved resistance to buckling which is provided by the strength of the helical coil 12.

Although FIG. 1 shows only a single coil 12, it is envisioned that the helical coil 12 might be made from two separate metal coils, one inside the other, that are wound in opposite directions (as shown in FIG. 2) so as to improve the strength of the sheath. FIG. 2 shows the distal end of a two coil sheath 11 which has an inner helical metal coil 17, an outer helical metal coil 13 both of which are finished with a straight distal end 15. FIG. 2 also shows a plastic covering 21 with a molded distal end 23 which design is similar to FIG. 1. A FIG. 2 type design in which the inner metal coil is nominally 2 mils thick, the outer metal coil is nominally 2 mils thick and the plastic covering is also 2 mils, would achieve a non-buckling sheath design which still has a significant wall thickness reduction as compared to sheaths that are currently available.

Since both FIG. 1 and FIG. 2 show sheaths that have metal coils, it is an intrinsic characteristic of metal to be radiopaque. Hence these sheath designs have the additional functions attribute of being radiopaque.

The possibility of a thin plastic coating or plastic tube on the interior surface of the inside metal coil is also envisioned for these sheath designs.

Although the utilization of sheaths in arteries is described herein in considerable detail, the sheath that is taught herein is also able to be used for access to a variety of lumens of humans or animals, such as veins, urethras, fallopian tubes or any similar vessel in a living body.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A sheath for introduction of catheters into a vessel of a living body comprising:

an inner core in the form of a flat wire helical metal coil having an exposed inner surface forming an inner lumen of the sheath, the flat wire helical metal coil consisting of a multiplicity of turns with adjacent turns being separated from each other so as to be non-contacting, the flat wire of said flat wire helical metal coil having a thickness between 1 and 5 mils and a width that is 5 to 50 times the metal thickness, a plastic covering surrounding the outer surface of said metal coil said plastic covering having an extension into the space between said adjacent turns of the metal coil, the inside diameter of said plastic extension being less than the outside diameter of the metal coil and being greater than or equal to the inside diameter of the metal coil; and, a plastic adapter operably joined to the proximal end of said helical coil and said plastic covering.

2. The sheath of claim 1 further comprising a sealing means placed in said plastic adapter to prevent blood leakage when the sheath is placed into an artery of the human body.

3. The sheath of claim 1 wherein said flat coil of said metal coil is made from stainless steel.

4. The sheath of claim 1 wherein said metal coil has a thickness of at least 0.002 inches and is at least as dense as stainless steel so as to make the sheath radiopaque.

5. The sheath of claim 1 wherein an inner coating of plastic is applied to said inner lumen.

6. The sheath of claim 1 wherein said inner helical metal coil is covered by an outer helical metal coil that is in turn covered by said plastic covering.

7. The sheath of claim 6 wherein said metal coils have collectively a thickness of of at least 0.002 inches with the metal of the metal coils being at least as dense as stainless steel so as to make the sheath radiopaque.

8. The sheath of claim 6 wherein said inner metal coil is coated on its interior surface with plastic.

* * * * *